US010220022B2

(12) United States Patent
Serbus et al.

(10) Patent No.: US 10,220,022 B2
(45) Date of Patent: *Mar. 5, 2019

(54) **COMPOSITIONS AND METHODS EMPLOYING *WOLBACHIA* FTSZ AS A TARGET FOR ALBENDAZOLE SULFONE**

(71) Applicant: The Regents of the University of California, Oakland, CA (US)

(72) Inventors: Laura Serbus, Santa Cruz, CA (US); Fredric Landmann, Santa Cruz, CA (US); Catharina Lindley, Santa Cruz, CA (US); Pamela White, Santa Cruz, CA (US); William Sullivan, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/041,433

(22) Filed: Jul. 20, 2018

(65) Prior Publication Data

US 2018/0333394 A1     Nov. 22, 2018

Related U.S. Application Data

(60) Continuation of application No. 15/232,515, filed on Aug. 9, 2016, now Pat. No. 10,028,936, which is a division of application No. 14/354,925, filed on Apr. 28, 2014, now Pat. No. 9,439,889, which is a continuation of application No. PCT/US2012/061088, filed on Oct. 19, 2012.

(60) Provisional application No. 61/553,214, filed on Oct. 30, 2011.

(51) Int. Cl.
| | |
|---|---|
| *A61K 31/4184* | (2006.01) |
| *A61K 31/404* | (2006.01) |
| *A61K 31/429* | (2006.01) |
| *A61K 31/428* | (2006.01) |
| *A61K 31/65* | (2006.01) |

(52) U.S. Cl.
CPC ........ *A61K 31/4184* (2013.01); *A61K 31/404* (2013.01); *A61K 31/428* (2013.01); *A61K 31/429* (2013.01); *A61K 31/65* (2013.01)

(58) Field of Classification Search
None
See application file for complete search history.

(56) References Cited

PUBLICATIONS

Bajpai et al., "Improvement in the efficacy of existing combination of antifilarials by inclusion of tetracycline in rodent model of brugian filariasis", Current Science, vol. 92, No. 5, 2007, 655-658.
Coulibaly et al., "A Randomized Trial of Doxycycline for Mansonella perstans Infection", New England Journal of Medicine, vol. 361, No. 15, 2009, pp. 1448-1458.
Hoerauf et al., "Filariasis in Africa-treatment challenges and prospects", Clinical Microbiology and Infection, vol. 17, No. 7, Jul. 2011, pp. 977-985.
Hoerauf et al., "Doxycycline as a novel strategy against bancroftian filariasia-depletion of Wolbachia endosymbionts ram Wuchereria bancrofti and stop of microfilaria production", Med Microbiol Immunol, 192(4), Nov. 2003, pp. 211-216.
McGarry et al., "Population dynamics of Wolbachia bacterial endosymbionts in Brugia malayi", Mol Biochem Parasitol, 135(1), May 2004, pp. 57-67.
PCT/US2012/061088, International Search Report and Written Opinion dated Feb. 28, 2013, 5 pages.
Rew et aL, "Screen for anthelmintics, using larvae of Ascaris suum", Am J Vet Res, 47(4), Apr. 1986, 869-874.
Sharma, R. et al Acta Tropica vol. 125, pp. 330-338, 2013.
Klarmann-Schulz U, et al. "Comparison of Doxycycline, Minocycline, Doxycycline plus Albendazole and Albendazole Alone in Their Efficacy against Onchocerciasis in a Randomized, Open-Label, Pilot Trial," Basáñez M-G, ed. PLoS Neglected Tropical Diseases. 2017;11(1):e0005156. doi:10.1371/journal.pntd.0005156.
Permi HS, et l. "Subcutaneous Human Dirofilariasis Due to Dirofilaria Repens: Report of Two Cases," Journal of Global Infectious Diseases. 2011;3(2):199-201. doi:10.4103/0974-777X.81702.

*Primary Examiner* — Heidi Reese

(74) *Attorney, Agent, or Firm* — Kilpatrick Townsend & Stockton LLP

(57) ABSTRACT

Compositions and Methods are described in which Albendazole sulfone binds to *Wolbachia* FtsZ providing anti filarial activity.

10 Claims, 6 Drawing Sheets

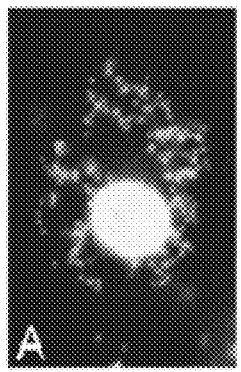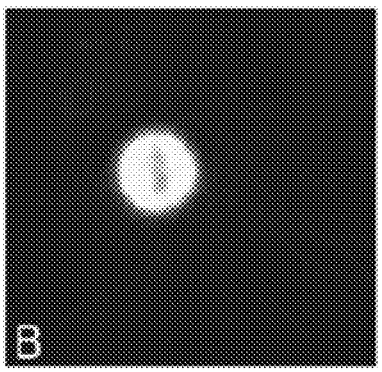
FIG. 1A    FIG. 1B
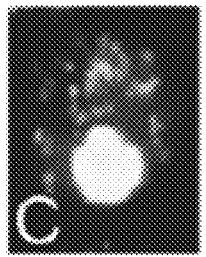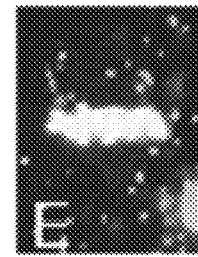
FIG. 1C    FIG. 1D    FIG. 1E    FIG. 1F

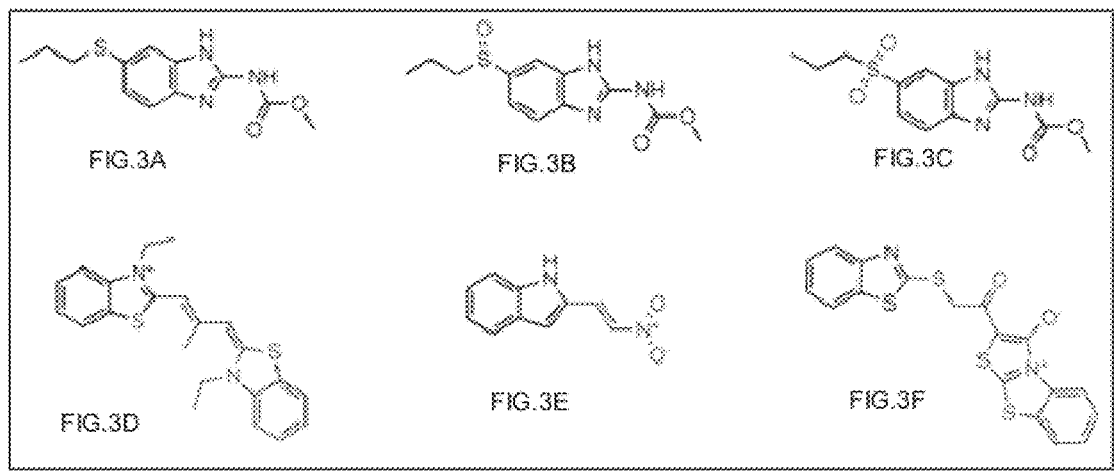
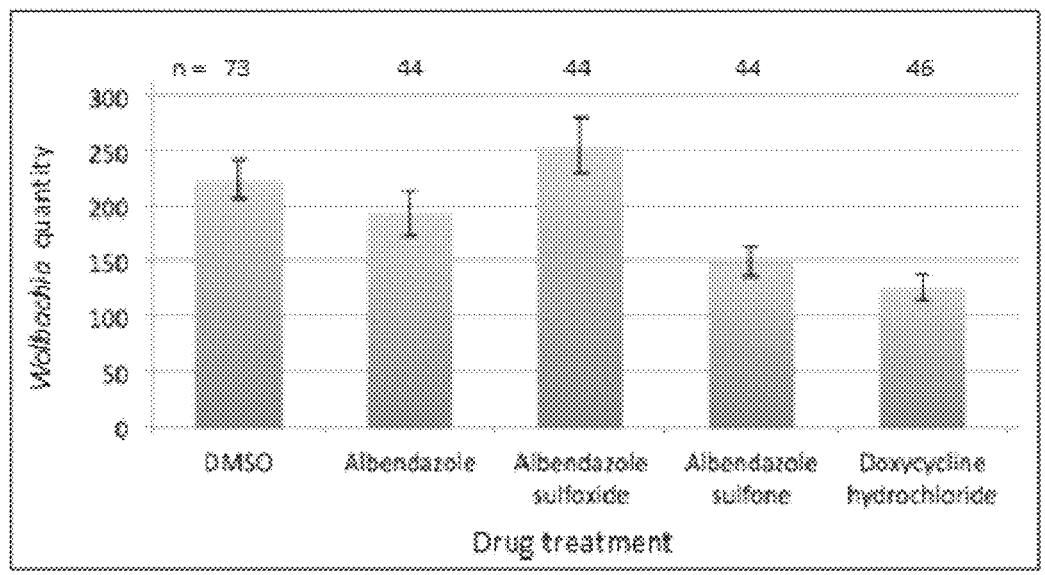
Fig.4

| mitotic phase | Wolb distribution | | "n" |
|---|---|---|---|
| | even | asymm | |
| prophase | - | 6 | 6 |
| prometaphase | 2 | 13 | 15 |
| metaphase | 4 | 8 | 12 |
| anaphase | - | 4 | 4 |
| telophase | 4 | 15 | 19 |
| total | 10 | 46 | 56 |

Fig. 7

COMPOSITIONS AND METHODS EMPLOYING *WOLBACHIA* FTSZ AS A TARGET FOR ALBENDAZOLE SULFONE

RELATION TO OTHER APPLICATIONS

This application claims priority to and the benefit of U.S. provisional application No. 61/553,214 filed 30 Oct. 2011 which is hereby incorporated by reference for all purposes.

FIELD OF THE INVENTION

The invention relates novel uses of drugs for treating filarial disease.

BACKGROUND

*Wolbachia* are obligate-intracellular, maternally transmitted bacteria. Antihelminthic drugs have been widely used to combat Lymphatic Filariasis and African River Blindness. A significant drawback of antihelminthic therapies currently used to treat River Blindness and Lymphatic filariasis is that they simultaneously target other nematode infections as well. This is a particular problem in areas where people are co-infected with *Loa loa* and either *O. volvulus* or *B. malayi*. In effort to identify new anti-*Wolbachia* therapeutics, we developed a *Wolbachia*-infected *Drosophila* cell line and conducted a high-throughput screen to identify compounds that reduced intracellular *Wolbachia* infection.

BRIEF DESCRIPTION OF THE INVENTION

Albendazole sulfone, a metabolite previously thought to be inactive, disrupts *Wolbachia* FtsZ, a key binary fission protein, in *Brugia malayi* nematodes associated with Lymphatic Filariasis.

SHORT DESCRIPTION OF THE FIGURES

The figures are shown and described as attached. The figures prove that Albendazole sulfone disrupts *Wolbachia* Fts Zin *Brugia malayi*.

FIG. 1A shows *Wolbachia* disruption in interphase of JE18 cells. FIG. 1B shows *Wolbachia* disruption in interphase of JW18TET cells. FIG. 1C shows *Wolbachia* disruption in prophase. FIG. 1D shows *Wolbachia* disruption in prophase. FIG. 1E shows *Wolbachia* disruption in metaphase. FIG. 1F shows *Wolbachia* disruption in late anaphase.

Figure 2:
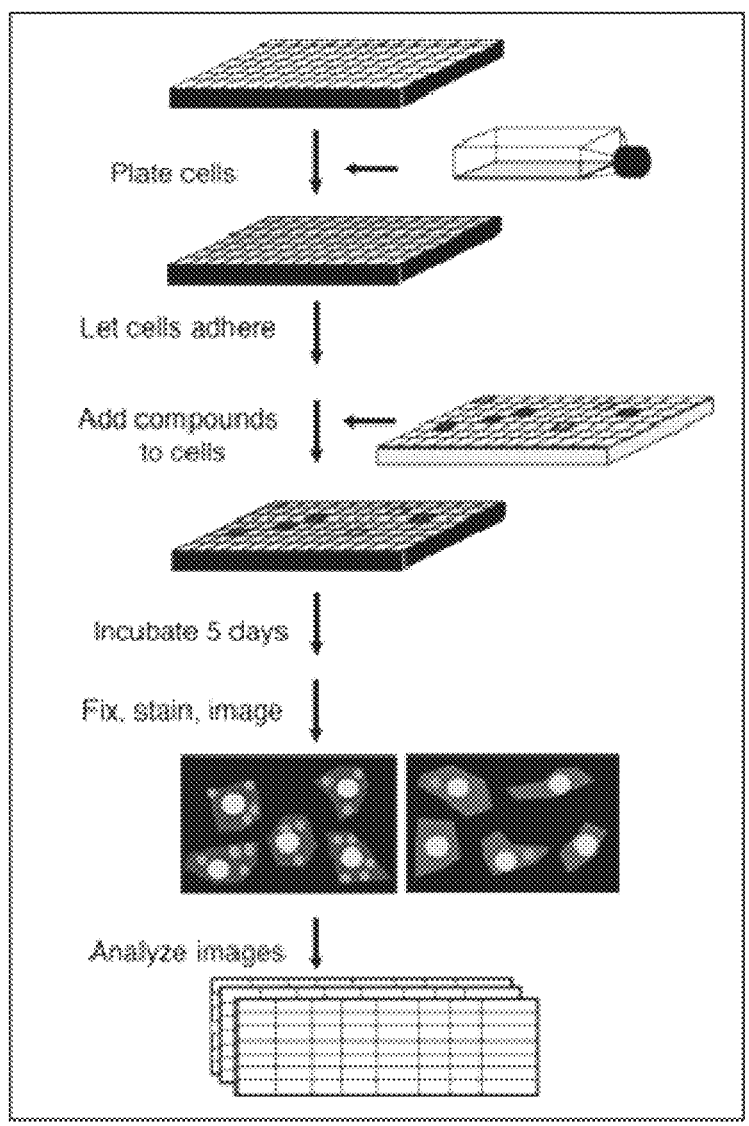

FIG. 2 Chemical screen method

FIG. 3A is Albendazole. FIG. 3B is Albendazole sulfoxide. FIG. 3C is Albendazole sulphone. FIG. 3D is NSC96932. FIG. 3E is NSC339601. FIG. 3F is NSC120982.

FIG. 4 Effect of Albendazole on *Wolbachia*

Figure 5A:
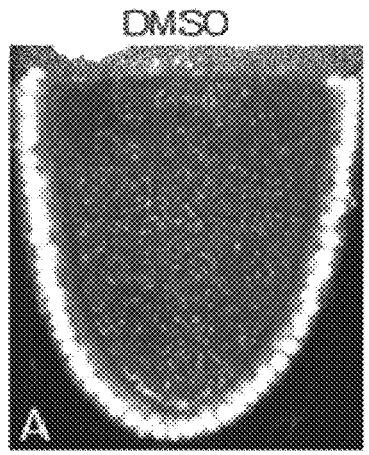
Figure 5B:
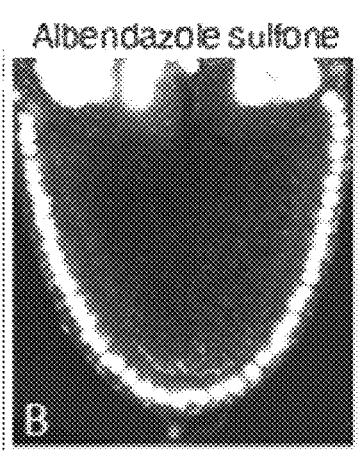
Figure 5C:
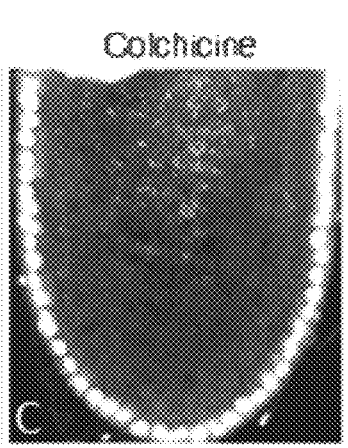
Figure 5D:
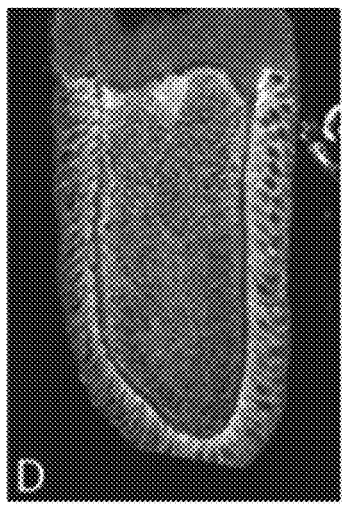
Figure 5E:
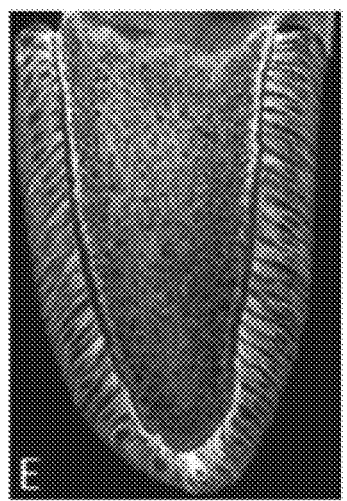
Figure 5F:
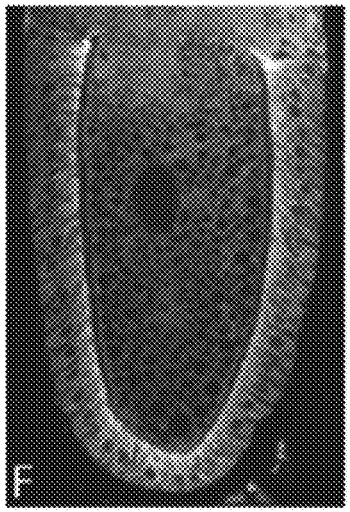

FIG. 5A shows stage 10A oocytes stained with Propidium iodide, treated with DMSO. FIG. 5B shows stage 10A oocytes stained with Propidium iodide, treated with Albendazole sulphone. FIG. 5C shows stage 10A oocytes stained with Propidium iodide, treated with colchicine. FIG. 5D shows stage 10A oocytes treated with anti-alpha tubulin and with colchicine. FIG. 5E shows stage 10A oocytes treated with anti-alpha tubulin and with Albendazole sulphone. FIG. 5F shows stage 10A oocytes treated with anti-alpha tubulin and with colchicine.

Figure 6:
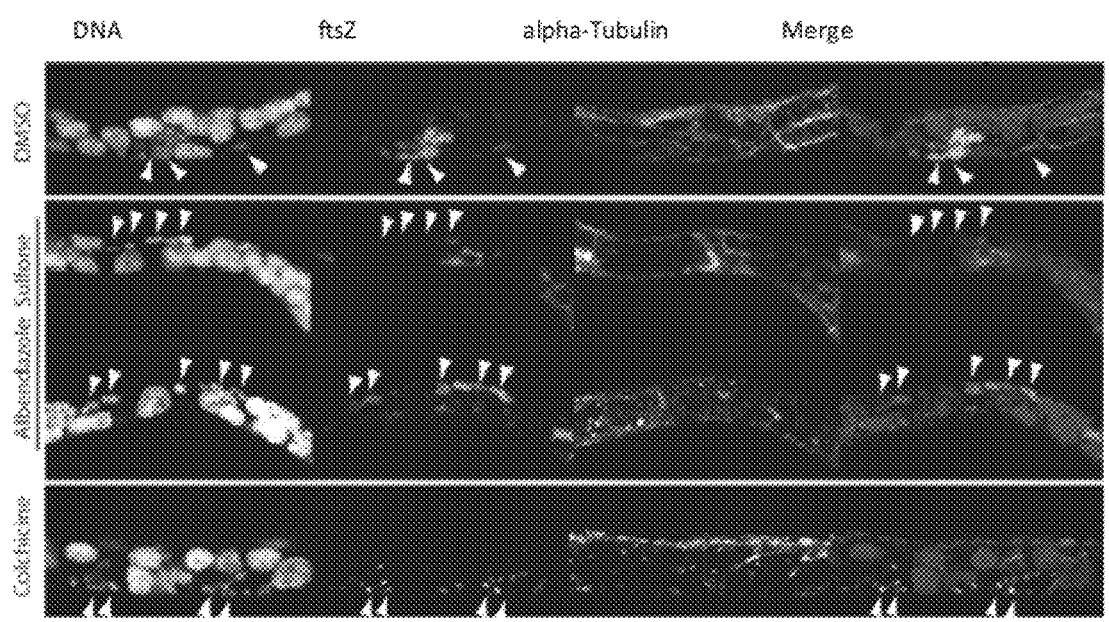

FIG. 6 *Wolbachia* disruption by Albendazole.

FIG. 7 Table showing asymmetric distribution of *Wolbachia* in mitotic cells

GENERAL REPRESENTATIONS CONCERNING THE DISCLOSURE

The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features.

This specification incorporates by reference U.S. provisional application No. 61/553,214 and all documents referred to herein and all documents filed concurrently with this specification or filed previously in connection with this application, including but not limited to such documents which are open to public inspection with this specification.

Where KCl is mentioned, this salt is used as an example only, and KCl may be substituted in all instances for any other monovalent salt.

DEFINITIONS

The following words and phrases are used herein as follows:

The terms "pharmaceutical formulation" and "pharmaceutical composition" mean any composition intended for administration to a human being or other mammal and comprises at least one drug; it may also include one or more other additives, for example pharmaceutically acceptable excipients, carriers, penetration enhancers, stabilizers, buffers or other materials.

The term "drug" means any substance that alters the physiology of an organism. Multiple drugs may be included in a single formulation.

The term "therapeutically effective amount" means an amount of a therapeutic agent, or a rate of delivery of a therapeutic agent, effective to facilitate a desired therapeutic effect.

The term "treatment" means the application of a process to an individual in order to alter a physiological state, whether or not the process includes a curative element.

"Controlled" release of a drug means release of the drug in a pre-determined or adjustable way such that the amount or rate or timing of release is pre-set or is altered in a desired way.

"Sustained" release of a drug means release over an extended period of time, for example minutes, hours or days. such that less than all the drug is released initially.

The term "subject" means any subject, generally a mammal (e.g., human, primate, canine, feline, equine, bovine, fish, birds etc in which management of a disease is desired.

DETAILED DESCRIPTION OF THE INVENTION

Wolbachia bacteria carried by filarial nematodes give rise to the neglected diseases African River Blindness and Lymphatic Filariasis in millions of people worldwide. In effort to identify new anti-Wolbachia therapies, we conducted a high-throughput chemical screen using Wolbachia-infected tissue culture cells. This screen yielded several compounds that resembled Albendazole, an antihelminthic drug used to treat millions of people with neglecte disease. Follow-up testing of Albendazole and its metabolites in Drosophila oogenesis showed that the metabolite Albendazole sulfone exerted anti-Wolbachia activity equivalent to Doxycycline. Immunostaining indicated that Albendazole sulfone treatment disrupts Wolbachia FtsZ, a key binary fission protein, in Brugia malayi nematodes associated with Lymphatic Filariasis. This highlights Albendazole sulfone as a potential new treatment for neglected disease as well as a starting point for developing a new class of anti-Wolbachia compounds Wolbachia are obligate-intracellular, maternally transmitted bacteria. They were initially studied because of the unconventional reproductive phenotypes they induce, namely sperm-egg cytoplasmic incompatibility, feminization of males, male-killing, and parthenogenesis. More recently, Wolbachia have become recognized as a major global health concern. Wolbachia are essential endosymbionts of filarial nematodes associated with the diseases Lymphatic Filariasis and African River Blindness that currently afflict 30 million people, with upwards of 400 million more at risk. Recent work indicated that the Wolbachia carried by these nematodes act as the causative agent of River Blindness and likely underlie much of the inflammatory reaction in Lymphatic Filariasis. This creates a need for effective anti-Wolbachia therapies to better address this major global health issue.

Antihelminthic drugs have been widely used to combat Lymphatic Filariasis and African River Blindness to date. These drugs directly target essential processes in the nematodes associated with these diseases, namely Onchocerca volvulus, Brugia malayi, and Wuchereria bancrofti. Ivermectin disrupts glutamate-gated chloride channels that control release of excretory/secretory vesicles that would normally suppress the immune response. Diethylcarbamazine is used to target the arachidonic acid pathway, shutting down a major metabolic pathway of the nematode. Albendazole is used to disrupt the nematode microtubule cytoskeleton. Orally administered Albendazole is rapidly metabolized by the liver into Albendazole sulfoxide and Albendazole sulfone. Albendazole sulfoxide is commonly referred to as the "active," antiparasitic form of Albendazole, while Albendazole sulfone is considered to be an inactivated form of the drug.

A significant drawback of antihelminthic therapies currently used to treat River Blindness and Lymphatic filariasis is that they simultaneously target other nematode infections as well. This is a particular problem in areas where people are co-infected with Loa loa and either O. volvulus or B. malayi. Loa loa migrates into the brain, and as such, general antihelminthic treatments cidal to Loa loa trigger a potentially lethal inflammatory cascade in the brain. The limitation on usage of antihelminthic treatments in these areas of co-infection creates a reservoir where filarial parasites can persist indefinitely. Targeting Wolbachia offers a means of distinguishing between these parasitic infections, as the nematodes that cause River Blindness and Lymphatic filariasis are reliant upon Wolbachia endosymbionts and Loa loa is not. Antibiotics such as Doxycycline are being used to address this treatment gap, though extended treatments are required for efficacy.

In effort to identify new anti-Wolbachia therapeutics, we developed a Wolbachia-infected Drosophila cell line and conducted a high-throughput screen to identify compounds that reduced intracellular Wolbachia infection. This screen yielded several Albendazole-like compounds. Follow-up testing of Albendazole and its metabolites in Drosophila oogenesis showed that the metabolite Albendazole sulfone exerted anti-Wolbachia activity equivalent to Doxycycline. Immunostaining indicated that Albendazole sulfone treatment disrupts Wolbachia FtsZ, a key binary fission protein, in the disease model B. malayi. This highlights Albendazole sulfone as a potential new treatment for neglected disease as well as a possible starting point for generating of a new class of specific anti-Wolbachia compounds.

Methods

Generation Cultured Cells

The JW18 cell line was generated as previously. Embryos were collected from Wolbachia-infected flies carrying a Jupiter-GFP transgene {Karpova, 2006 #129}, then homogenized and plated in flasks. During the next six months of maintenance, a subset of flasks converted into immortal tissue culture lines, including the JW18 cell line. A cured version of the JW18 line was made by treating the cells with Tetracycline at 100 ug/mL for one month.

Screening Approach

Cells were plated in 384-well, clear bottom plates (Griener Bio-one) pre-coated with 0.5 mg/mL Concanavalin A. JW18 cells were added to 22 columns, and JW18TET cells were added to the remaining 2 columns at a dilution of 6500 cells per well. After the cells adhered to the plates, compounds were transferred into 20 columns of JW18 cells in the center of the plate using a Janus MDT pin tool. The final concentration of compound was 100 uM per well. All treatments were distributed into 3 plate replicates.

After a 5-day incubation with the compounds at 25 C, the cells were prepared for imaging. Cells were fixed for 20 minutes in 4% formaldehyde and rinsed with PBS using an automated BioTek liquid handler. All staining solutions were administered using a Multidrop robot, with extensive rinsing between treatments. The primary antibody, mouse anti histone (MAB052, Millipore), was used at 1:1250 in PBS/0.1% Triton. Secondary antibody goat anti-mouse Alexa 594 (Invitrogen) was used at 1:1250. DAPI was used as a saturated solution, diluted to a final concentration of 1:40. After staining, PBS+Azide was added to all wells of the plates.

Screen Data Analysis

Stained treatment plates were imaged using the MetaExpress Micro system (Molecular Devices, Sunnyvale Calif.). 10 images were acquired per well at 40× magnification. These images were next analyzed using customized journaling software provided by Molecular Devices. The journal first masks any areas where clumps of cells are detected, based upon intensity of the Jupiter-GFP. The boundaries of the remaining cells and their nuclei are recognized based upon the Jupiter-GFP and anti-histone stains. A mask is applied to the nuclei, to obscure the hi stone and DAPI signal from those areas. A threshold for DAPI fluorescence detection is set to detect as much Wolbachia as possible in JW18 control cells while minimizing detection of background DAPI signal in JW18TET control cells. Then this cytoplasmic DAPI level, read to indicate *Wolbachia*, is scored in the cytoplasm of individual cells to determine whether each cell is infected with *Wolbachia*. The cutoff value distinguishing "infected" from "uninfected" cells is 4000-5000 fluorescence units per cell. This is considered to be a low cutoff limit, as some infected cells exhibit over 100,000 cytoplasmic DAPI fluorescence units.

A spreadsheet from the journal indicates the quantity of *Wolbachia*-infected cells versus total cells measured in each well. A Z' factor is calculated for each plate based upon the average frequency of cell infection for JW18 and JW18TET control cells. Our Z' factors per plate range from 0.2 to 0.65. An initial hit range is calculated to lie between the JW18 average infection frequency−3 standard deviations, and the average JW18TET infection frequency+3 standard deviations. To further refine identification of hits, we also calculated an average infection frequency for all JW18 cells on the plate (treated or not), as most treatment wells are expected to be indistinguishable from untreated controls. Wells are that lie within 3 standard deviations of the mean are exluded, and remaining wells are classified as hits within that replicate. Hit wells that are identified in at least 2 out of 3 replicates are considered to be finalized hits.

Drug feeding conditions: Fly feeding we done as previously described.

Staining: *Drosophila* Ovary staining was done with with PI, anti-tubuli. *Drosophila* Embryo staining was done with with anti-FtsZ. *Brugia* microfilarial staining was done with with PI, anti-tubulin, and anti-FtsZ.

Results

Development of a *Drosophila* Cell Line Constitutively Infected With *Wolbachia*

To identify compounds that affect intracellular *Wolbachia* titer, we first generated *Drosophila* tissue culture cells that are constitutively infected with *Wolbachia*. The cell line used for this study, JW18, is amenable to high throughput screening in that it expresses a Jupiter-GFP fusion protein that binds host microtubules {Karpova, 2006 #129}. *Wolbachia* are carried within 88% or more of the host cell population (n=1053 cells scored). Comparing JW18 to Tetracycline-cured JW18 cells showed no significant difference in mitotic index, with a frequency of 0.27% observed for JW18 and 0.68% for JW18+Tet (n=1867 and 2339, respectively). Additionally, no significant difference was observed in the frequency of binucleate cells between JW18 (9.1%, n=873) and Tetracycline-cured JW18 cells (10.5%, n=1081). Thus, *Wolbachia* do not exert an obvious influence on progression of the host cell cycle in the JW18 cells.

To test whether *Wolbachia* exhibit normal interactions with the host cell, bacterial localization patterns were examined in the JW18 cell line. In interphase cells, many *Wolbachia* were closely juxtaposed with Jupiter-GFP-labeled microtubules (FIG. 1A-B). Live imaging indicated that *Wolbachia* can move processively along those interphase microtubules (Supplementary Movie 1), consistent with earlier reports of *Wolbachia*-microtubule interactions. In mitotic cells, *Wolbachia* were asymmetrically distributed throughout the cytoplasm 82% of the time (n=56, FIG. 1C-F, Suppl Table 1), reminiscent of *Wolbachia* localization patterns observed in embryonic and larval neuroblasts {Albertson, 2009 #127}. These data indicate that *Wolbachia* distribution in the JW18 cell line is consistent with that of intact *Drosophila* tissues.

Identification of *Wolbachia*-reducing compounds by high-throughput screening. The JW18 cells were implemented in a high-throughput screen to identify anti-*Wolbachia* compounds. High-throughput screening is a well-established approach for testing chemicals and RNAi molecules against a variety of cell types. In this screen, 3081 compounds froth the National Cancer Institute were used. The collection included structurally and functionally diverse synthetic compounds as well as a set of natural products. Cells were incubated for 5 days with each compound, then fixed, stained, and imaged using automated robotics (FIG. 2). Customized analysis software was used to compare the images from compound-treated wells to the control cells to assay for significant changes in the quantity of *Wolbachia*-infected cells. All treatment plates were run in triplicate.

From this screen, 23 preliminary candidate anti-*Wolbachia* compounds were identified. These compounds reduced the *Wolbachia*-infection frequency into the hit range in at least 2 out of 3 replicates tested, and also fell outside the range of 98.5% of the data (Suppl Table 2). A number of these hits have previously been implicated as having antimicrobial activity, consistent with what would be expected from the screen. Two compounds, Cinerubin B and Mitomycin B are structural derivatives of the anticancer antibiotics Daunorubicin and Mitomycin, which are approved by the FDA for use as chemotherapy agents. NSC207895 is a DNA damaging agent. Pyronin B is a quaternary ammonium compound, many of which serve as the antimicrobial agents in commercial disinfectants. One other compound, NSC96932 has also been shown in a prior screen to exert antibacterial activity against *Streptococcus pyrogenes*.

To investigate the basis for the anti-*Wolbachia* activity of the antibacterial NSC96932 compound, we examined its chemical structure. This revealed that NSC96932 is a benzthiazole sharing some structural similarity with Albendazole, the widely used antihelminthic drug known for disrupting microtubules (FIG. 3). Examining the structural features of all other hits in our screen indicated that two additional anti-*Wolbachia* compounds that share structural similarity to Albendazole, the benzthiazole NSC150982 and the benzimidazole NSC339601. This implies that Albendazole-like compounds share a common anti-*Wolbachia* activity.

*Wolbachia* Titer in *Drosophila* is Reduced by Albendazole Sulfone

As Albendazole is already a widely used, FDA-approved drug, we proceeded to test it and the primary metabolites Albendazole sulfoxide and Albendazole sulfone for anti-*Wolbachia* effects in *Drosophila* oogenesis. This system provides a high-precision method for assessing *Wolbachia* titer in a well-characterized developmental context. After a 24-hour treatment period, *Wolbachia* counts from single oocyte focal planes indicated that Albendazole-treated flies had 194+/−20 *Wolbachia* per oocyte, and Albendazole sulfoxide exhibited 255+/−27 *Wolbachia* per oocyte, which was not significantly different from the DMSO treated control (225+/−18 *Wolbachia* per oocyte, FIG. 4A). However, Albendazole sulfone-treated oocytes had significantly less *Wolbachia* than the control, with 150+/−13 *Wolbachia* evident per oocyte. This matched the *Wolbachia* depletion seen in Doxycycline-treated oocytes, which exhibited 126+/−11 *Wolbachia* (FIG. 4A). Thus, Albendazole sulfone exhibits a significant anti-*Wolbachia* effect in *Drosophila*.

Albendazole sulfone affects *Wolbachia* titer in a microtubule-independent manner. Albendazole and structurally similar benzimidizoles like Nocodazole are thought to disrupt microtubule polymerization by binding to beta-tubulin. As prior work in *Drosophila* indicates that *Wolbachia* titer is at least partially dependent upon host microtubules, a role for Albendazole sulfone in reducing *Wolbachia* titer initially appears sensible. However, prior mutant studies have identified key amino acids within beta tubulin that are important for response to benzimidazoles. In particular, N165 and Y200 are thought to form a hydrogen bond, stabilizing the structure of the beta-tubulin, restricting accessibility to a benzimidazole binding site. Most *Drosophila* beta tubulins carry these residues, and thus are not predicted to be susceptible to benzimidazoles. This presents a puzzle as to the basis for the *Wolbachia*-reduction effect of Albendazole sulfone.

To address whether Albendazole sulfone acts on *Wolbachia* by disrupting the oocyte microtubule cytoskeleton, a combination of approaches was used. It has previously been shown that *Wolbachia* concentrate at the oocyte posterior cortex in a microtubule-dependent manner. In this study, posterior *Wolbachia* localization was seen in 95% of DMSO controls and 93% of Albendazole sulfone-treated oocytes (n=56 and n=46, respectively) (FIG. 6A-B). This differed significantly from Colchicine-treated oocytes, where only 21% exhibited posterior *Wolbachia* localization (p<0.001, n=13, FIG. 6C). We also examined the cytoskeleton directly by immunolabeling the microtubules. DMSO controls and Albendazole sulfone-treated oocytes exhibited fibrillar microtubule arrays, while the cytoplasm of Colchicine-treated oocytes was devoid of filamentous structure (FIG. 5D-F). This demonstrates that Albendazole sulfone does not affect the overall orientation or structure of the oocyte microtubule cytoskeleton. This suggests that Albendazole sulfone acts upon Wolbachia in a microtubule-independent manner.

Albendazole Sulfone Acts Against *Wolbachia* FtsZ

An alternative target for Albendazole sulfone may be FtsZ, a bacterial protein critical for cell wall assembly during binary fission. FtsZ is thought to be a homolog of eukaryotic tubulin. Alignment of FtsZ sequence with tubulin suggests that FtsZ should be susceptible to disruption by benzimidazole treatments (FIG. 5). Prior studies also indicate that Albendazole-like compounds can target and disrupt FtsZ function in *Escherichia coli* and *Mycobacterium tuberculosis*.

To investigate whether Albendazole sulfone disrupts *Wolbachia* FtsZ, we fed this compound to *Brugia malayi* microfilariae, which carry *Wolbachia* as an essential endosymbiont. Unlike DMSO controls, the Albendazole sulfone treatment triggered widespread disruption of *B. malayi* microtubules. This is consistent with the predicted benzimidazole susceptibility of *B. malayi* beta tubulin (FIG. 5). Interestingly, FtsZ was also disrupted in most of the Albendazole sulfone-treated microfilariae, indicating that this compound compromises both *Brugia* microtubules and *Wolbachia* FtsZ.

In view of the above the inventors posed the questions: By what mechanism does Albendazole sulfone act against *Wolbachia* FtsZ? And is FtsZ disruption a consequence of host microtubule disassembly, or due to a separate effect on FtsZ by Albendazole sulfone? Examination of Albendazole-sulfone-treated microfilariae revealed instances in which microtubules were disrupted and FtsZ was not (FIG. 6). To further test whether *Wolbachia* FtsZ relies on host microtubules, we also treated *Brugia* with the microtubule-disrupting drug Colchicine. Though this treatment severely disrupted host microtubules, FtsZ remained concentrated near Wolbachia DNA (FIG. 6). This indicates that host microtubules are not required for FtsZ localization in *Wolbachia*. Rather, the data suggest that Albendazole sulfone targets *Wolbachia* FtsZ and host microtubules separately in *Brugia* microfilariae.

Discussion

This study has redefined the mechanism of action used by Albendazole, an antihelmenthic drug that is used to treat millions worldwide with neglected disease. High-throughput screening indicated that several Albendazole-like compounds reduce *Wolbachia* infection in tissue culture. Further tests of Albendazole sulfone, a metabolite previously thought to be inactive, triggered significant reductions of *Wolbachia* titer in *Drosophila* oogenesis. Furthermore, Albendazole sulfone treatment of *Brugia malayi*, the filarial nematode associated with Lymphatic Filaraisis, yielded disruptive effects against both *Brugia* microtubules and *Wolbachia* FtsZ, an essential binary fission protein. This positions Albendazole as a potentially useful tool to use in tandem with Doxycycline for River Blindness and/or Lymphatic Filariasis prevention.

A function for Albendazole sulfone is surprising as this molecule was previously described as inactive (Gottschall G W et al 1990). This determination may have been made in part because the Albendazole sulfone metabolite is less abundant in human serum and urine than Albendazole sulfoxide. A study testing competitive inhibition of tubulin polymerization also showed Albendazole sulfone to be a far less potent disrupter of beta-tubulin than Albendazole sulfoxide. This former drawback for Albendazole sulfone may now elevate its usefulness for treating African River Blindness and Lymphatic filariasis, as a lower potency of host microtubule disruption would be expected to reduce non-specific filarial targeting, while ante FtsZ activity would simultaneously provide a more specific anti-*Wolbachia* effect.

This study suggests that Albendazole sulfone could serve as a starting point for generating of a new class of anti-*Wolbachia* compounds for treating neglected disease. Other benzimidazoles previously approved by the FDA have some drawbacks. Thiabendazole was found to be teratogenic, and thus its usage has been discontinued. Mebendazole is microfilaricidal, and thus not amenable to areas where patients are co-infected with *Loa loa*. Flubendazole functions well as a macrofilaricide while leaving microfilariae undisturbed, thus positioning it well for usage in areas with *Loa loa* co-infection. The drawback of Flubendazole is that it needs to be administered by injection. in order to function effectively.

The possibility of Albendazole-sulfone-based drug development raises the question of how specifically such compounds may target *Wolbachia* FtsZ rather than FtsZ in other bacterial strains. Broad-spectrum antibacterials quickly give rise to resistance genes, and this is a particular concern for *M. tuberculosis*, which has become extremely drug resistant in some areas. Comparing FtsZ between bacteria indicates considerable variation in the amino acid sequence, suggesting that strain-specific FtsZ targeting may be possible. For example, FtsZ in *D. melanogaster Wolbachia* and *Brugia malayi Wolbachia* are 92% identical, but FtsZ from *Wolbachia*, *M. tuberculosis* and *E. coli* share only 42-45% sequence identity.

The divergence of FtsZ sequences in different bacteria may allow for selection of inhibitors with substantially varied composition as well. It has been shown that *M. tuberculosis* FtsZ was unaffected by Albendazole, while an Albendazole-like compound could significantly disrupt FtsZ. Moreover, extensive variation on the benzimidazole structure is evident when comparing FtsZ-disrupting compounds picked up by non-biased high-throughput screening.

Even a benzthiazole related to the hits NSC96932 and NSC339601 from our screen has been shown to exhibit FtsZ-disrupting activity. This openness of FtsZ to structurally diverse permutations of benzimidazole creates the potential to design narrow spectrum anti-FtsZ compounds for targeting *Wolbachia* and other types of bacteria.

Future structural characterization FtsZ molecules from *Wolbachia* and other bacterial species will aid substantially to design new narrow-spectrum drugs. Modeling of a putative benzimidazole binding site has been done, based upon site-specific mutations in beta tubulin that control benzimidazole susceptibility. Oddly, these residues are predicted to be buried within the center of the beta-tubulin structure. Kinetic studies have definitively shown that benzimidazoles bind beta tubulin and disrupt microtubule stability, however. One explanation to reconcile these findings is that an interdomain movement within beta-tubulin exposes these key residues to enable benzimidazole binding. This binding site could be amenable to benzimidazole variants ranging widely in size, as even Albendazole sulfoxide, a relatively small benzimidazole, remains partly exposed to solvent when wedged into the predicted binding pocket of beta tubulin. Thus, armed with detailed understanding of FtsZ structure, the side arms of new benzimidazoles could be designed to permit compound binding to FtsZ substrates of specific types of bacteria while excluding others.

The invention claimed is:

1. A method for targeting *Wolbachia* bacteria in a subject, the method comprising administering to the subject a formulation comprising Albendazole sulfone.

2. The method of claim 1 wherein the formulation is administered to the subject orally.

3. The method of claim 1 wherein the formulation is administered to the subject intravenously, intramuscularly or subdermally.

4. The method of claim 1 wherein the formulation is a sustained release formulation.

5. The method of claim 1 wherein the formulation further comprises one or more pharmaceutically acceptable excipients, carriers, penetration enhancers, stabilizers or buffers.

6. The method of claim 1 further comprising administering to the subject a Doxycycline compound.

7. The method of claim 1, wherein the formulation is a controlled release formulation.

8. The method of claim 1, wherein the formulation disrupts *Wolbachia* FtsZ in a disease model comprising *B. malayi*.

9. The method of claim 1, wherein the subject is co-infected with *Loa Loa*.

10. The method of claim 1, wherein the administration kills the *Wolbachia* bacteria in the subject.

* * * * *